United States Patent [19]

Lamoreux

[11] Patent Number: 4,534,364
[45] Date of Patent: Aug. 13, 1985

[54] SAGITTAL KNEE TEST APPARATUS

[76] Inventor: Larry W. Lamoreux, 5470 Manila Ave., Oakland, Calif. 94618

[21] Appl. No.: 533,365

[22] Filed: Sep. 19, 1983

[51] Int. Cl.³ .............................................. A61B 6/00
[52] U.S. Cl. ..................................... 128/774; 128/782
[58] Field of Search .................... 128/774, 782; 73/379

[56] References Cited

U.S. PATENT DOCUMENTS

| T100,602 | 5/1981 | Roley et al. | 128/782 |
| 4,037,480 | 7/1977 | Wagner | 128/774 X |
| 4,323,080 | 4/1982 | Melhart | 128/774 |

FOREIGN PATENT DOCUMENTS

| 858452 | 7/1949 | Fed. Rep. of Germany | 128/774 |
| 2912981 | 10/1980 | Fed. Rep. of Germany | 128/774 |
| 839493 | 6/1981 | U.S.S.R. | 128/774 |

OTHER PUBLICATIONS

Daniel et al., "Instrumented Drawer Testing", pp. 1–4.
Townsend et al., "Total Motion Knee Gonieretry", J. Biomechanics, vol. 10, No. 3, 1977, pp. 183–193.

Primary Examiner—Edward M. Coven
Attorney, Agent, or Firm—Bielen and Peterson

[57] ABSTRACT

Apparatus for measuring ligamentous insufficiency in the knee, the apparatus including a leg support having an adjustment mechanism for disposing the legs at a select test angle and having straps securing the ankles and the thighs to the leg support; an instrument bridge having mounting supports for mounting the bridge to the tibia, the bridge having at one end an indicator with a patella contact for measuring displacements of the patella and femur relative to the tibia; and a push-pull force applicator for applying posterior and anterior forces to the lower leg to induce sagittal excursions.

16 Claims, 8 Drawing Figures

SAGITTAL KNEE TEST APPARATUS

BACKGROUND OF THE INVENTION

This invention relates to apparatus for measuring ligamentous insufficiency in the knee to enable a physican to provide a diagnosis of injury and evaluation of different treatment methods. In the past, abnormal motion between the tibia and the femur was detected by a physcan by manipulation of the leg by hand. Often the motion of a leg with a ligament tear is subtle and difficult to compare with the patient's uninjured leg. Because even a normal knee may have a substantial motion, it is desirable to quantitatively measure the displacement to allow an accurate comparison between the patient's normal and injured knees to determine the extent of injury.

While an electromechanical instrument has been devised for measuring the anterior drawer in the legs of normal volunteers and patients with known anterior cruciate deficits in a clinical research study, the device has certain disadvantages. The instrument is expensive and bulky and is not autoclavable to allow for its use in the operating room. Also the instrument is primarily restricted to the 20° anterior drawer (Lachman) test.

The apparatus of this invention is autoclavable and is designed for use in both the 20° anterior draw and 90° anterior draw tests and without refitting is designed for use in measuring posterior excursions. It is believed that measurement of both anterior and posterior excursions provides the physician with the maximum useful data for proper diagnosis and treatment.

SUMMARY OF THE INVENTION

The sagittal knee test apparatus of this invention is devised to accurately measure displacements in the knee particularly for determining and treating ligamentous insufficiencies. The apparatus includes a leg support frame having an adjustment mechanism for disposing the legs of a patient at a select test angle. The leg support frame includes ankle straps and thigh straps for securing the patient's legs to the frame at two fixed points which permit displacements at the knee to be measured in reference to these fixed points.

Operating in conjunction with the leg support frame is an instrument bridge having two mounts positioned against the tibia and secured thereto by legs straps. The instrument bridge, is displaced from and aligned along the length of the tibia with a telescoping end with an indicator positionable over the patella. The indicator comprises a spring-loaded plunger with an end button that is pressed against the patella. The indicator detects and records displacements at the end of the bridge with respect to the patella.

To induce these displacements, a push-pull load applicator is used. The preferred load applicator comprises a crooked hand probe with a spring scale to register the force of push or pull applied to the anterior or posterior of the lower leg proximate the knee. An electronic pressure sensitive transducer can be substituted for the spring indicator if an electronic or electronically displayed reading is desired. The applied force from the load applicator displaces the tibia relative to the femur. As the patella is assumed to move in unison with the femur, the plunger, which is in contact with the patella, is displaced with respect to the end of the bridge which is in contact with the tibia. The displacement is transmitted to the indicator for both a posterior and anterior thrust such that the sagittal component of knee laxity is accurately measured. The indicator for simplicity is mechanical. However an equivalent electronic display and/or displacement measuring means may be used.

The load applicator is an independent device from the instrument bridge and can be used alone by the physican for preliminary diagnostics where a definite applied force is desired, but an accurate measurement is not required. Similarly, the instrument bridge can be used in conjunction with some other means of applying a displacement force that is not the same in construction as that described as a preferred embodiment.

DETAILED DESCRIPTION OF THE PREFERRED EMBODIMENT

Figure 1:
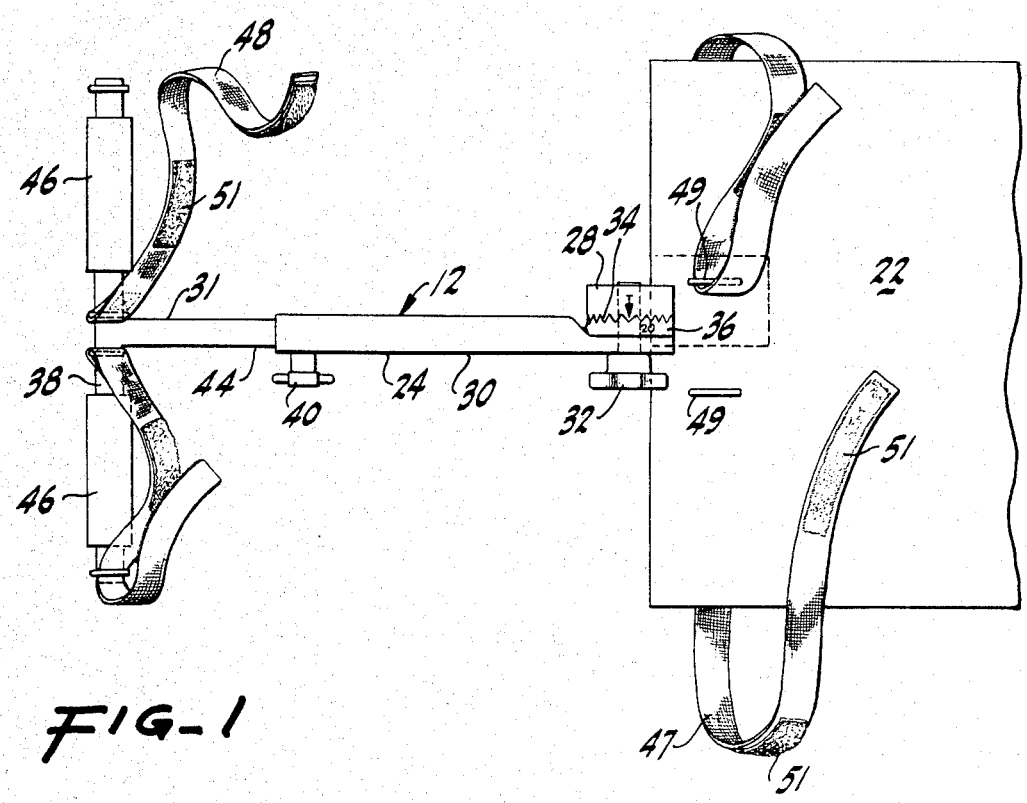
FIG. 1 is a top view of the leg support component of the saggital knee test apparatus.
Figure 2:
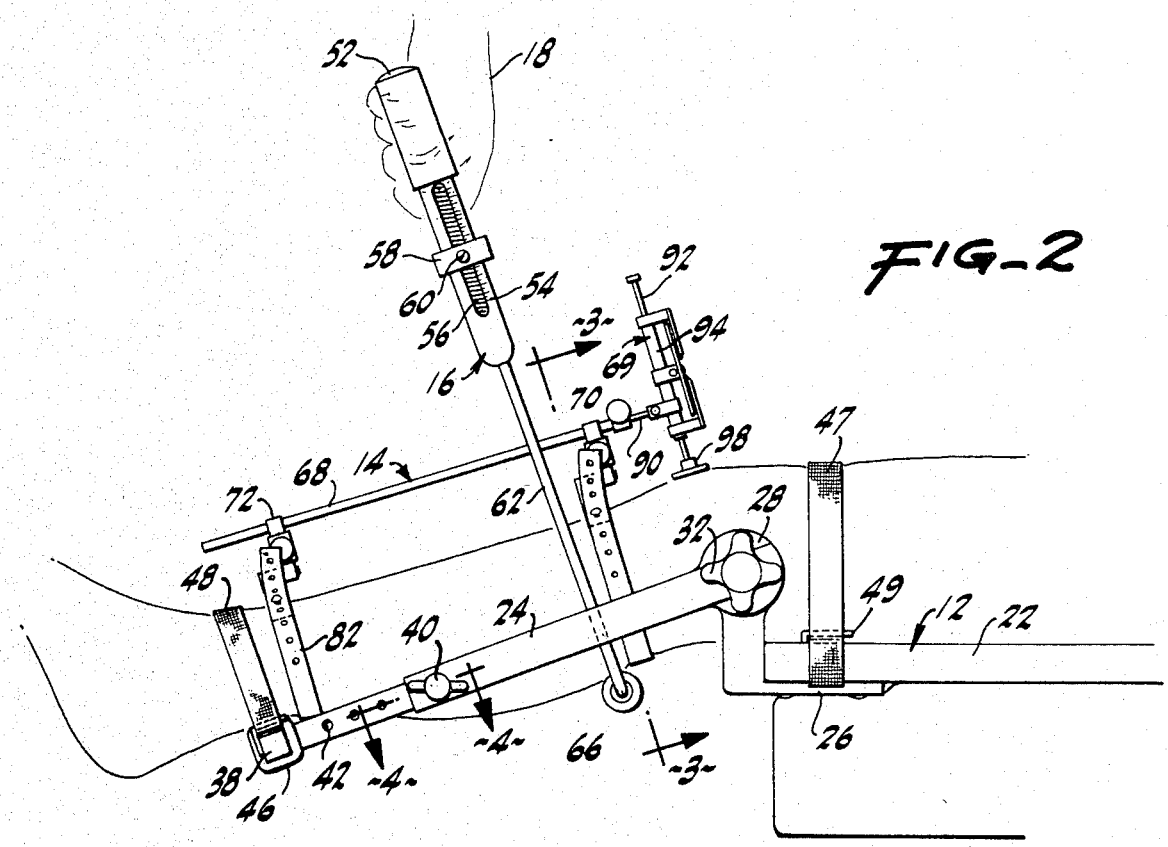
FIG. 2 is a side elevational view of the three component knee test apparatus in a demonstrated use.

Referring to the drawings, in particular to FIGS. 1, 2, 3, and 7, the sagittal knee test apparatus comprises three components, a leg support 12, a measurement device 14 and a force applicator 16. The apparatus is shown in use with a physcan 18 and patient 20 illustrated in part in phantom, in FIG. 2.

The leg support 12 comprises a base pad 22, which is placed on an examining table. The base pad 22 has a leg support frame 24 connected to a coupling plate 26 at the front of the pad 22 by an adjustment clamp 28. The leg support frame 24 has a central support arm 30 and a telescoping T-member 31 at the distal end of the support arm 30 for support of the legs at the ankles. Angular disposition of the support arm 30 relative to the base pad 22 is obtained by loosening the clamping screw 32 and rotating the support arm 30 to the position desired. The toothed clamp faces 34 insure that the position is accurately selected and maintained without slippage. In the standard tests for knee laxity, two positions are used, a 20° flexion for the Lachman Test and a 90° flexion for the Drawer Sign Test. The former 20° position is optimal for testing a suspected anterior cruciate ligament tear, and the latter 90° position is optimal for testing a suspected posterior cruciate ligament tear. These two positions are indicated by markings 36 on the adjustment clamp 28.

Figure 4:
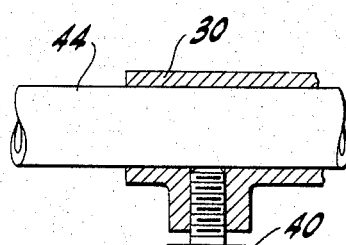
FIG. 4 is a partial cross sectional view of the leg support component taken on the lines 4—4 in FIG. 2.
Figure 3:
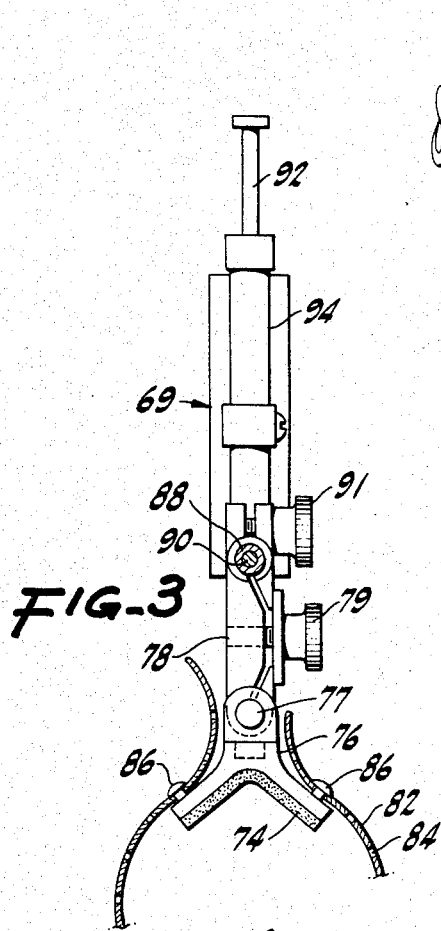
FIG. 3 is a cross sectional view of the measuring device component taken on the lines 3—3 in FIG. 2.

The telescoping T-member 31 at the end of the support arm is extendable to accomodate different patients with different length legs. The crosspiece 38 on the T-member is positioned to contact the back of the ankle at a location above the heel where the heel tendon joins the calf muscle. The position is fixed by insertion of a threaded clamp 40 which engages the neck piece 44 of the T-member 31 as shown in FIG. 4. In addition to a proper positioning mechanism, the crosspiece 38 preferably includes padded sleeves 46 to assure a maximum degree of comfort during the test period.

Since the ankle contact at the crosspiece 38 of the T-member 31 is essentially the pivot point for inducing deflection of the tibia at the knee, to accomplish both anterior and posterior tests, thigh straps 47 and ankle straps 48 are necessary to maintain the position of the lower legs, particularly during the anterior test where a force is applied against the back of the leg below the knee. The thigh straps 47 and ankle straps 48 loop through retainer hooks 49 on the base pad 22 and overlap to engage a hook and mat coupling means 51.

The force is applied with a push-pull force applicator 16. The applicator has a handle 50 with a hand grip 52 and a spring scale 54 with a compression spring 56 and slide collar 58 with an engagement screw 60 for engaging the spring 56 at a selected position for a desired force. Projecting from the handle 50 is a hook shaped probe 62 having a transverse pressure bar 64. The probe 62 slidably extends into the handle 50 and is locked to the slide collar 58 by the engagement screw 60. A rubberlike contact pad 66 is mounted on the pressure bar 64. The contact pad has a convex surface for contacting the back of the leg during a leg pull for anterior tests, and a concave surface for contacting the front of the leg during a leg push for posterior tests. Since excursions of the tibia at its connection with the femur are being measured, the force is applied against the tibia just below the knee.

Figure 5:
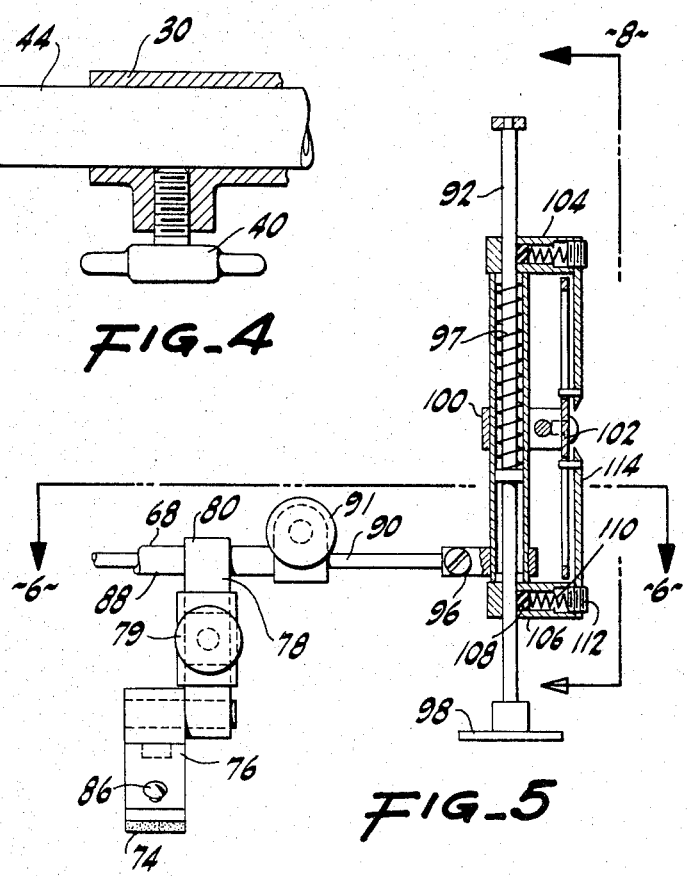
FIG. 5 is an enlarged side elevational view, partially in cross section, of the measuring device component.
Figure 6:
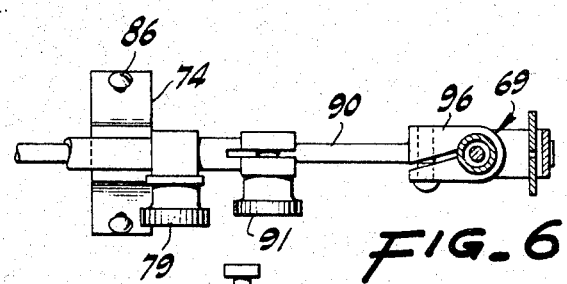
FIG. 6 is a partial cross sectional view taken on the lines 6—6 in FIG. 5.
Figure 8:
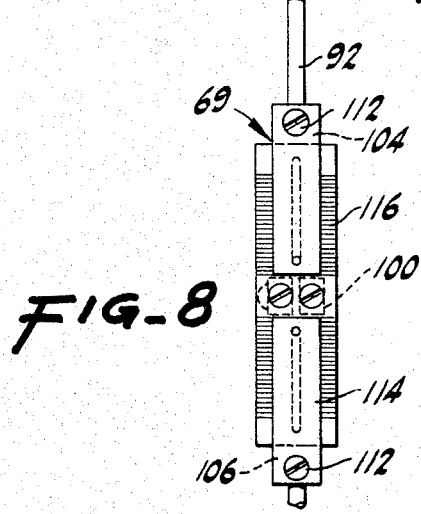
FIG. 8 is a view of the indicator taken on the lines 8—8 in FIG. 5.
Figure 7:
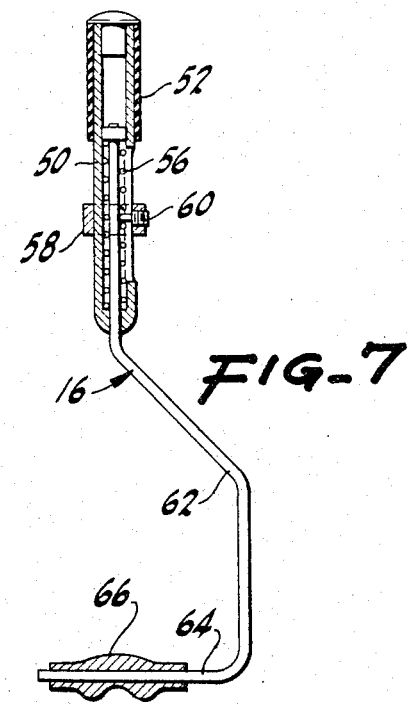
FIG. 7 is a cross sectional view of the force application component of the knee test apparatus.

The movement of the tibia relative to the femur is measured and recorded by the measurement device 14, which comprises an instrument bridge 68 and supported displacement instrument 69, shown also in FIGS. 5 and 6. The instrument bridge is constructed with a mounting support 70 proximate the knee and a mounting support 72 distally displaced from the knee and an interconnecting tube 88. The mounting supports 70 and 72 include a shallow V-shaped contact pad 74 having a projecting post 76 with a clamp stud 77. A double clamp 78 engaging the clamp stud 77 at one end and the tube 88 at the other end, utilizes a center mounted clamp screw 79 to secure the supports to the elongated tube. The contact pad 74 rests against the anterior of the tibia and is strapped thereto by an elastic strap 82 having strap holes 84 through which a pin 86 is inserted to hold the end of a strap wrapped around the patient's leg. The tube 88 is substantially aligned with the tibia by the supports to permit a telescoping rod 90, projecting from a rod clamp 91, to position the displacement instrument 69 over the patient's patella.

The displacement instrument 69 is constructed with a rod-like plunger 92 reciprocally slidable in a plunger barrel 94 that is fastened perpendicularly to the end of the rod 90 by a yoke fastener 96. The plunger barrel contains a spring 97, to spring load the plunger 92 to lightly press a flat button 98 at the end of the plunger, against the patella. Connected to the barrel by a fastener 100 is a scale card 102 having an incremental millimeter scale.

The plunger projects from each end of the barrel, and carries two slide indicators 104 and 106 to record the relative displacement of the plunger, which is in contact with the patella, with the barrel, which is in contact with the tibia.

At the start of a test, the two indicators are positioned against the respective ends of the barrel indicating zero displacement.

In a posterior force test, the tibia is pushed causing the barrel to shorten the distance between the barrel and the patella button. The lower indicator 106 is pushed down the plunger until maximum displacement is reached. When the force against the tibia is relaxed, the barrel retracts leaving the indicator on the plunger to record the displacement. The indicator remains at its displaced position by friction engagement of a shoe 108 that is biased by a spring 110 contained in a hole, capped by a set screw 112. A pointer 114 on the indicator 106 points to the scale marking 116 on the card to indicate the displacement that occurred.

Similarly, in an anterior force test, the tibia is pulled causing the barrel to rise on the plunger carrying the top indicator 104 upward. When the force is relaxed the indicator remains on the plunger at the point of maximum displacement. When a test is repeated, the pertinent indicator, or both indicators are returned to a zero start position.

Because simple mechanical parts are utilized the entire apparatus can be sterilized in an autoclave. The elements are easily disassembled for repair or packing, and are simple in construction and operation. The modular construction permits easily observable confirmation of results and permits recognition of equipment malfunction or dislocation that would impair the accuracy of the results.

The apparatus is designed for use with patients having a variety of different physical builds, and provides for adjustment of the apparatus to conform to the patient. Further, the force applicator is adjustable to permit the application of measurement forces other than a 20 lb standard test force, which has been shown to be inadequate to produce maximum displacement for certain larger patients.

While in the foregoing embodiments of the present invention have been set forth in considerable detail for the purposes of making a complete disclosure of the invention, it may be apparent to those of skill in the art that numerous changes may be made in such detail without departing from the spirit and principles of the invention.

What is claimed is:

1. Sagittal knee test apparatus comprising:
   a. a leg support mechanism for supporting a patient's leg in a select angular position;
   b. a hand held, manual force applicator adapted for selectively applying on anterior or posterior displacement force against the upper portion of the patient's tibia; and
   c. a mechanical measuring device having a support structure with means for fastening said support structure to the anterior aspect of the patient's tibia, and a displacement instrument mounted to said support structure over the patient's patella, said displacement instrument including:
      1. a contact member adapted to contact the patient's patella,
      2. a coupling means for displaceably coupling said contact member to said support structure with said contact member being maintained in contact with the patella, and,
      3. indicator means for indicating relative displacements between said coupling means and said contact member corresponding to relative displacements between said tibia and said patella upon application of anterior and posterior forces to the tibia by said force applicator.

2. The knee test apparatus of claim 1 wherein said leg support mechanism comprises a support frame having a support arm with an adjustable coupling means for coupling said arm to a seat structure at a selected angular disposition, said support frame having further a crosspiece connected to said arm adapted to support thereon the patient's legs proximate the ankles.

3. The knee test apparatus of claim 2 wherein said crosspiece includes ankle straps for retaining the patient's ankles against the crosspiece.

4. The knee test apparatus of claim 2 wherein said support frame includes a seat pad connected to said coupling means.

5. The knee test apparatus of claim 1 wherein said force applicator includes means for measuring push and pull forces applied to the patient's tibia.

6. The knee test apparatus of claim 2 wherein said coupling means comprises an adjustment clamp.

7. The knee test apparatus of claim 2 wherein said crosspiece has a connected neck piece telescopically engageable with said support arm.

8. The knee test apparatus of claim 2 wherein said force applicator includes means for measuring push and pull forces applied to the patient's tibia.

9. The knee test apparatus of claim 8 wherein said measuring means comprises a spring scale.

10. The knee test apparatus of claim 1 wherein said contact member comprises a plunger and said coupling means comprises a plunger barrel reciprocally receiving said plunger.

11. The knee test apparatus of claim 10 wherein said plunger barrel includes spring bias means for maintaining said contact member against the patient's patella.

12. The knee test apparatus of claim 10 wherein said indicator means comprises marker means on said plunger cooperating with said barrel to indicate displacements of said barrel relative to said plunger.

13. The knee test apparatus of claim 12 wherein said barrel has two open ends and said plunger extends from both open ends, said marker means comprising displaceable indicators slidably coupled to said plunger and displaceable by contact with the ends of said barrel, said barrel having a scale card mounted thereon to indicate the position of said slide indicators.

14. The knee test apparatus of claim 13 wherein said displaceable indicators each include a spring loaded friction shoe contacting said plunger for maintaining the displaced position of said indicators when displacement forces are withdrawn.

15. The knee test apparatus of claim 1 wherein said support structure of said measuring device comprises an instrument bridge having first and second mounting supports adapted for mounting against the upper and lower part of the patient's tibia, an elongated element connecting said supports and arranged longitudinal to and displaced from said tibia, said elongated element having an end with a fastener element for mounting said displacement instrument to said elongated element.

16. The knee test apparatus of claim 15 wherein said fastening means for fastening said support structure to the tibia comprises elastic straps connected to said first and second mounting supports.

\* \* \* \* \*